United States Patent
Nakamura et al.

(10) Patent No.: US 6,271,425 B1
(45) Date of Patent: Aug. 7, 2001

(54) PROCESS FOR PRODUCING ALCOHOLS

(75) Inventors: Eiichi Nakamura, 5-3-3-1001, Honkomagome, Bunkyo-ku, Tokyo 113-0021; Masaya Sawamura, Tokyo, both of (JP)

(73) Assignees: Fujisawa Pharmaceutical Co., Ltd., Osaka; Eiichi Nakamura, Tokyo, both of (JP)

( * ) Notice: Subject to any disclaimer, the term of this patent is extended or adjusted under 35 U.S.C. 154(b) by 0 days.

(21) Appl. No.: 09/355,345

(22) PCT Filed: Feb. 4, 1998

(86) PCT No.: PCT/JP98/00453
§ 371 Date: Oct. 8, 1999
§ 102(e) Date: Oct. 8, 1999

(87) PCT Pub. No.: WO98/34893
PCT Pub. Date: Aug. 13, 1998

(30) Foreign Application Priority Data

Feb. 6, 1997 (JP) .................................................. 9-023905

(51) Int. Cl.[7] .......................... C07C 29/00; C07C 29/132; C07C 33/30; C07C 33/28; C07C 35/22
(52) U.S. Cl. .......................... 568/811; 548/542; 549/354; 549/355; 549/420; 549/497; 568/813; 568/815; 568/818; 568/838; 568/852
(58) Field of Search ...................................... 568/811, 813, 568/815, 818, 838, 852; 548/542; 549/354, 355, 420, 497

(56) References Cited

PUBLICATIONS

Sawamura et al., Conversion of Alkyl Halides, etc.; Synlett, (7), 801–802, Jul. 1997.*

Nakamura et al., J. Am. Chem. Soc., 113, 8980–8982, 1991.*

Mayer et al., Tetrahedron Letters, vol. 37, No. 18, pp. 3117–3120, 1996.*

* cited by examiner

*Primary Examiner*—Peter O'Sullivan
(74) *Attorney, Agent, or Firm*—Oblon, Spivak, McClelland, Maier & Neustadt, P.C.

(57) ABSTRACT

A novel process for producing alcohols, characterized by reacting an organic halide represented by the formula R—X (wherein R means an organic residue and X means a halogen atom) with oxygen molecules in the presence of an organotin compound and a reducing agent and optionally in the presence of a free-radical inhibitor in an amount up to 0.3 equivalent based on the organic halide to obtain an alcohol represented by the general formula R—OH (wherein R has the same meaning as the above).

8 Claims, No Drawings

PROCESS FOR PRODUCING ALCOHOLS

TECHNICAL FIELD

This invention relates to a novel process for producing alcohols and is useful in chemical and pharmaceutical fields.

BACKGROUND ART

The reaction utilizing the carbon radical formed from an organohalogen compound is important in organic synthesis as a means for constructing a cyclic skeleton by way of carbon—carbon linkage but, in many instances, the radical on the carbon skeleton is reduced by a hydrogen donor, which eliminates the functional group.

On the other hand, the inventors reported previously that an alcohol can be provided by capturing the alkyl radical intermediate formed from an alkyl halide in the presence of $Bu_3SnH$ and AIBN (2,2'-azobisisobutyronitrile) with molecular oxygen. This technology is instrumental in organic synthesis as a means for directly substituting a hydroxyl group for a halogen atom on a carbon skeleton. Meanwhile, Prandi and coworkers obtained a similar result by reacting a substrate halide with 0.05~0.1 equivalent of $Bu_3SnCl$, 1 equivalent of the radical reaction promoter AIBN and 6 equivalents of $NaBH_4$ in hot ethanol under bubbling with air (Tetrahedron Letters, vol. 37, pages 3117–3120, 1996).

However, those methods also have aspects to be improved for application to large-scale reactions in that the halide which can be a substrate is limited to highly reactive compounds such as alkyl iodides, allyl bromide and benzyl bromide and that the reaction requires either 2 equivalents of an organotin compound or 0.05~0.1 equivalent of an organotin compound plus 1 equivalent of the unstable AIBN and, in addition, requires a large excess of oxygen as well.

DISCLOSURE OF THE INVENTION

Having been dedicated to solving the above problems, the inventors of this invention discovered that when the reaction is conducted in the presence of a reducing agent, as well as sodium iodide where necessary, which regenerates the organotin compound in the course of reaction, the objective alcohol can be provided in high yield using only a catalyst amount of the organotin compound and no more than a substantially stoichiometric amount of molecular oxygen in the absence of a radical initiator, which is unstable, or in the presence of only a very minor amount of the initiator. They have accordingly perfected the instant invention.

The novel process for producing alcohols according to this invention comprises reacting an organohalogen compound (I) of the following formula

$$R\text{—}X \tag{I}$$

(wherein R represents an organic residue and X represents halogen) with molecular oxygen in the presence of an organotin compound and a reducing agent, either in the absence of a radical initiator or in the presence of not more than 0.3 equivalent of a radical initiator based on said organohalogen compound to give an alcohol (II) of the following formula:

$$R\text{—}OH \tag{II}$$

(wherein R has the same meaning as defined above).

The novel process for producing alcohols in accordance with this invention is industrially more advantageous than the conventional production technology in that the use of a radical initiator, which is unstable and involves risks for hazards in mass handling, can be completely dispensed with or limited to a very low level, that the requirements of an organotin compound, which is also toxic, are no more than the catalyst amount, and that since the reaction condition is more or less neutral, the reaction can be carried out even in the presence of various functional groups. Furthermore, since the objective alcohol can be provided in high yield by using oxygen only in a substantially stoichiometric ratio to the substrate organohalogen compound, the process is also useful for reducing the cost of synthesis of labeled compounds which requires an expensive oxygen isotope.

This invention is now described in detail.

The organohalogen compound as the substrate to which this invention can be applied is not particularly restricted. In this invention, the halogen can be replaced with a hydroxyl group only provided that the carbon atom to which the halogen is attached has an $sp^3$ hybrid orbital. Furthermore, as will be apparent from the working examples presented hereinafter, the carbon atom bound to the halogen may be any of primary, secondary and tertiary carbons.

Therefore, the structure of the organic residue R of the organohalogen compound (I) is not particularly restricted but includes lower alkyl groups containing 1~6 carbon atoms (e.g. methyl, ethyl, etc.), higher alkyl groups containing 7~20 carbon atoms (e.g. heptyl, octyl, nonyl, bicyclo [5.2.0]nonyl, decyl, undecyl, dodecyl, tridecyl, adamantyl, etc.), lower alkenyl groups containing 3~6 carbon atoms (e.g. allyl, 2-butenyl, etc.), higher alkenyl groups containing 7~20 carbon atoms (e.g. 2-heptenyl, 3-octenyl, etc.), ether compound residues, ar(lower) alkyl groups (e.g. benzyl, benzhydryl, trityl, etc.), saccharide residues (e.g. glucose, galactose and other monosaccharide residues; sucrose, lactose and other oligosaccharide residues, etc.), amino acid residues, sulfide compound residues and amide compound residues, among others.

Those organic residues may contain functional groups which do not interfere with the reaction. For example, even compounds containing hydroxyl groups as functional groups can be used as the substrate of this invention without prior protection. Moreover, this reaction can be applied even to compounds containing an ester, lactone or amide function without any trouble provided that $NaBH_3CN$ is used as the reducing agent.

It should, of course, be understood that any organohalogen compound having a structure which will completely inhibit this reaction cannot be used as the substrate.

The foregoing is a matter which can be readily understood by those skilled in the art and, therefore, defining the substrate as "organohalogen compound" herein will not introduce ambiguity into this invention.

In this connection, when the substrate has a carbon-carbon double bond in an appropriate position within the molecule, there are cases in which the alkyl radical intermediate formed on removal of the halogen does not react directly with molecular oxygen but adds itself to the carbon-carbon double bond first to form a ring and the carbon radical formed de novo thereupon reacts with molecular oxygen to give the alcohol. Such cases also fall within the scope of this invention. Specific examples are given hereinafter in Table 2.

The halogen X in organohalogen compound (I) includes chloro, iodo, bromo, etc. but iodo is the most preferred halogen for purposes of this invention.

When the halogen is chloro or bromo and the progress of reaction is retarded, the oxygenation can be allowed to proceed with improved efficiency by conducting the reaction in the presence of 1~3 equivalents of sodium iodide. Moreover, when a primary halide is used as the substrate, the yield can be enhanced dramatically by conducting the reaction in the presence of perfluorodecalin.

The "organohalogen compound (1)" mentioned above can be prepared by any one skilled in the art, starting with a known compound and following a synthetic process per se known.

The "organotin compound" to be used in this invention includes but is not limited to organotin hydrides and organotin halides, preferably trialkyltin halides (e.g. tributyltin chloride, dibutyl(t-butyl) tin chloride, etc.), and triaryltin halides (e.g. triphenyltin chloride etc.).

The amount of the "organotin compound" to be used in this invention may be no more than a catalyst amount but is preferably 0.005~0.5 equivalent, more preferably 0.05~0.2 equivalent, based on the organohalogen compound (I).

The "reducing agent" for use in this invention includes but is not limited to borohydrides (e.g. sodium borohydride, lithium borohydride, zinc borohydride, sodium cyanoborohydride, sodium acetoxyborohydride, etc.).

In the practice of this invention, the "reducing agent" is preferably used in an amount of not less than 2 equivalents, more preferably 2~5 equivalents, still more preferably 2~3 equivalents, based on the substrate organohalogen compound (I).

The reaction according to this invention can be carried out using various solvents which do not interfere with the reaction, such as alcohols (e.g. ethanol, isopropyl alcohol, butanol, t-butanol, etc.), BTX, and ethers (e.g. tetrahydrofuran etc.), inclusive of mixtures thereof, among others. Particularly preferred are alcohols.

The reaction temperature for use in this invention is not particularly restricted provided that the radical reaction is enabled to proceed, although the reaction is preferably conducted under warming, more preferably at 30~70° C., most preferably 55~65° C.

The introduction of oxygen to the reaction system in this invention can be effected in the routine manner and may be effected whether in an open system or in a closed system. More preferably, the oxygen is supplied in the form of a mixed gas consisting of oxygen and an inert gas such as nitrogen (oxygen: inert gas=1:1~1:7, preferably 1:1~1:4, approx.).

The larger the available amount of oxygen is, the greater is the extent to which the catalyst "organotin compound" is deactivated. Therefore, it is advisable, for minimizing the "organotin compound" requirements, to react oxygen in a proportion of 1~3 equivalents, more preferably 1~2 equivalents, most preferably 1.5 equivalents, based on the substrate "organohalogen compound".

As the available amount of oxygen in the reaction system is increased, the "radical chain" is terminated so that unless the radical initiator is added in a large amount, the reaction ceases to proceed so that the operation on a high-production scale can hardly be carried through. This invention is characterized in that the reaction is carried out in the presence of 1~3 equivalents of oxygen, and as the amount of oxygen is thus restricted, the organotin compound requirements are reduced and, as a consequence, the "radical initiator" requirements are also reduced drastically or even to nil.

While radical reactions are generally carried out in the presence of a "radical initiator", the outstanding feature of this invention is that the reaction can be carried out substantially without using the "radical initiator" which is unstable and involves risks for hazards in mass handling.

However, since the presence of 0.3 equivalent or less, preferably 0.005~0.3 equivalent, of a "radical initiator" based on the substrate organohalogen compound (I) may sometimes result in acceleration of the reaction and/or inhibition of by-production of the reduced compound, the "radical initiator" can be added, where necessary, in the amount defined above. In particular, the use of a radical initiator is recommended when the organohalogen compound is a primary iodide.

The "radical initiator" in this context includes but is not limited to AIBN and dibenzoyl peroxide.

Furthermore, even when oxygen is used in excess of 3 equivalents based on the organohalogen compound, the reaction can be carried out with improved efficiency by adding the organotin compound and radical initiator each in a proportion of 0.1 equivalent or more, preferably about 0.2 equivalent.

The reaction according to this invention is preferably conducted with intense stirring in order that the oxygen will be sufficiently dissolved in the reaction mixture. The preferred intensity of stirring is equivalent to not less than 800 rpm, more preferably not less than 1000 rpm.

The reaction conditions of this invention have been described above. In conducting a specific reaction, it is necessary to optimize the reaction conditions according to the structure of organohalogen compound (I) and the species and amount of the organotin compound, among other variables, but such optimization is a matter which can be made easily by any one skilled in the art.

The following examples illustrate this invention in further detail.

EXAMPLE 1

A reaction vessel (50 ml, a two-neck, eggplant type flask) is subjected to nitrogen gas purging. NaBH$_3$CN (1.0 mmol, 62.8 mg), AIBN (0.005 mmol, 0.8 mg) and Bu$_2$(t-Bu)SnCl (0.025 mmol, 8.1 mg, 7 µl) are added to tert-butanol (2 ml). Then, 3-iodo-1-phenylheptane (0.5mmol, 151.1mg, 115 µl) is added. The introduction of nitrogen gas is discontinued, a nitrogen gas-filled black butyl rubber balloon is set instead, and using a syringe, oxygen (0.75 mmol, 18 ml) is bubbled into the solution. Thereafter, the reaction vessel is immersed in an oil bath at 60° C. After 13 hours, heating is discontinued and the reaction mixture is diluted with pure water (10 ml) and extracted with ether (15 ml×4). The organic solution is dried over anhydrous magnesium sulfate and the solvent is distilled off. The residue is purified by column chromatography (silica gel 4 g, ethyl acetate/hexane 20%) to provide 1phenyl-3-heptanol (89.4 mg, 93%).

IR (neat, cm$^{-1}$): 3362, 3062, 3026, 2930, 1603, 1496, 1455, 1043, 747, 699

$^1$H NMR (CDCl$_3$, 200 MHz, δ): 0.90 (t, J=6.9 Hz, 3H) 1.20–1.89 (m, 8H), 2.65 (ddd, J=9.5, 9.6, 14.3 Hz, 1H), 2.81 (ddd, J=6.7, 9.5, 14.3 Hz, 1H), 3.57–3.71 (m, 1H), 7.20–7.49 (m, 5H)

$^{13}$C NMR (CDCl$_3$, 100 MHz, δ): 14.04, 22.72, 27.77, 32.06, 37.27, 39.07, 71.37, 125.76, 128.37, 128.38, 142.21

GC-Mass (EI): m/e 192.20 (M$^+$)

The results of experiments applying the reaction of this invention using various species of organohalogen compound (I) in otherwise the same manner as Example 1 are summarized below (Table 1, Table 2).

TABLE 1

$$R-X + O_2 + NaBH_3CN \xrightarrow[t\text{-BuOH, 60° C.}]{\substack{R_3SnCl\ (5\ mol\ \%)\\ AIBN\ (1\ mol\%)}} R-OH + R-H$$

1a–j    1.5 eq    2 eq                         2a–j    3a–j

| entry | (1) | $R_3SnCl$ | time, h | (2) | yield of $2$,[a] % | ratio of $2:3$[b] |
|---|---|---|---|---|---|---|
| 1 | $C_{10}H_{21}-I$ (1a) | $Bu_3SnCl$ | 16 | $C_{10}H_{21}-OH$ (2a) | 68 | 70:30 |
| 2[c] | 1a | $Bu_3SnCl$ | 14 | 2a | 93 | 93:7 |
| 3 | 1a | $Bu_2(t\text{-Bu})SnCl$ | 19 | 2a | 82 | 91:9 |
| 4 | 1b (sugar iodide: I-CH2-pyranose with OMe, OAc, OAc, OAc) | $Bu_3SnCl$ | 19 | 2b (corresponding alcohol HO-CH2-pyranose) | 77 | 84:16 |
| 5 | 1b | $Bu_2(t\text{-Bu})SnCl$ | 11 | 2b | 88 | 91:9 |
| 6[d] | $C_{12}H_{25}-Br$ (1c) | $Bu_2(t\text{-Bu})SnCl$ | 12 | $C_{12}H_{25}-Br$ (2c) | 90 | 93:7 |
| 7[e] | THPO-(CH2)4-Cl (1d) | $Bu_2(t\text{-Bu})SnCl$ | 16 | THPO-(CH2)4-OH (1d) | 75 | f |
| 8 | Ph-CH=CH-CH2-Br (1e) | $Bu_2(t\text{-Bu})SnCl$ | 16 | Ph-CH=CH-CH2-OH (2e)[g] | 85 | f |
| 9 | $4\text{-}CH_3C_6H_4CH_2\text{-}Br$ (1f) | $Bu_2(t\text{-Bu})SnCl$ | 18 | $4\text{-}CH_3C_6H_4CH_2\text{-}OH$ (1f) | 63 | f |
| 10 | Ph-CH2CH2-CH(Bu)- (1g, as 3-methyl? PhCH2CH2CH(Me)Bu) | $Bu_3SnCl$ | 19 | Ph-CH2CH2-C(OH)(Bu)- (2g) | 92 | 93:7 |
| 11 | 1g | $Bu_2(t\text{-Bu})SnCl$ | 10 | 2g | 92 | 93:7 |
| 12 | bicyclic lactone with I and CO2Me (1h) | $Bu_3SnCl$ | 18 | bicyclic lactone with OH and CO2Me (1h), trans:cis = 2:1[h] | 60 | 93:7 |
| 13 | $C_7H_{15}$-CH(OH)-CH(CH3)-CH2OH (1i) | $Bu_2(t\text{-Bu})SnCl$ | 12 | $C_7H_{15}$-CH(OH)-CH(OH)-CH2OH (1i) | 56 | 95:5 |
| 14 | 1-iodoadamantane (1j) | $Bu_3SnCl$ | 18 | 1-hydroxyadamantane (2j) | 94 | 96:4 |
| 15 | 1j | $Bu_2(t\text{-Bu})SnCl$ | 20 | 2j | 96 | 97:3 |

[a]Isolated yield.
[b]Determined by $^1$H NMR of crude product.
[c]3 equiv of perfluodecaline was added.
[d]2 eq of NaI was added.
[e]1d was first converted to the corresponding iodide with 2 eq of NaI and then conversion to the alcohol in one-pot-procedure.
[f]Not determined.
[g]Obtained as a mixture with PhCH(OH)CH—CH$_2$ in a ratio of 85:15.
[h]Determined by $^1$H NMR of purified product.

TABLE 2

| entry | (1) | time, h | (2) | yield of 2,[a] % |
|---|---|---|---|---|
| 1 | (1k) | 20 | (2k) trans:cis = 2:3:1[b], 1:1[b] | 85 |
| 2 | (1l) | 27 | (2l) trans:cis = 2:3:1[b], 1:1 | 83 |
| 3 | (1m) | 22 | (2m) | 83 |

Reaction: $1k\text{-}m + O_2 + NaBH_3CN \xrightarrow{Bu_3SnCl\ (5\ mol\ \%),\ AIBN\ (1\ mol\ \%)}_{t\text{-BuOH},\ 60°\ C.} 2k\text{-}m + 3k\text{-}m$ (1.5 eq O₂, 2 eq NaBH₃CN)

[a]Isolated yield.
[b]Determined by ¹H NMR of purified product.

EXAMPLE 2

A reaction vessel (50 ml, a two-neck, eggplant type flask) is subjected to nitrogen gas purging. Tert-butanol (2 ml) is added and freeze-degassing is performed twice. Under nitrogen, AIBN (0.005 mmol, 0.8 mg), NaBH$_3$CN (1.0 mmol, 62.8 mg), Bu$_2$(t-Bu)SnCl (0.025 mmol, 8.1 mg, 7 μl) and 3-iodo-1-phenylheptane (0.5 mmol, 151.1 mg, 115 μl) are added, in a single dose, to the reaction vessel. After quick freeze-degassing, the reaction mixture is dissolved in warm water at about 30° C. to 40° C. . The supply of nitrogen gas is discontinued and a nitrogen gas-filled black butyl rubber balloon is set instead. An oxygen isotope ($^{18}O_2$, 99 atom %) from a bombe is collected into a measuring cylinder through water displacement and a (1.0 mmol, 24 ml) fraction of the oxygen is bubbled into the solution using a syringe. The reaction vessel is then immersed in an oil bath at 60° C. After 11 hours, heating is discontinued and the reaction mixture is diluted with pure water (10 ml) and extracted with ether (15 ml×4). The organic solution is dried over anhydrous magnesium sulfate and the solvent is distilled off. The residue is purified by column chromatography (silica gel 4 g, ethyl acetate/hexane 20%) to provide 1-phenyl-3-($^{18}O$)heptanol (95.2 mg, 98%) [$^{16}OH$ not detected by GC-MS (EI)].

IR (neat, cm$^{-1}$): 3344, 3062, 3026, 2930, 1604, 1496, 1455, 1031, 989, 747, 699

¹H NMR (CDCl$_3$, 400 MHz, δ): 0.90 (t, J=6.9 Hz, 3H), 1.20–1.89 (m, 8H), 2.65 (ddd, J=9.5, 9.6, 14.3 Hz, 1H), 2.81 (ddd, J=6.7, 9.5, 14.3 Hz, 1H), 3.57–3.71 (m, 1H), 7.20–7.49 (m, 5H)

¹³C NMR (CDCl$_3$, 100 MHz, δ): 14.03, 22.72, 27.77, 32.06, 37.27, 39.07, 71.34, 125.76, 128.37, 128.38, 142.22

GC-Mass (EI): m/e 194.20 (M+) (192.2 ($^{16}O$-compound, M$^+$) was not detected).

The results of experiments applying the reaction of this invention using various species of organohalogen compound (I) in otherwise the same manner as Example 2 are summarized below (Table 3).

TABLE 3

$$R\text{—}I + *O_2 + NaBH_3CN \xrightarrow[t\text{-BuOH, 60°C}]{Bu_2(t\text{-Bu})SnCl\ (5\ mol\ \%)\ AIBN\ (1\ mol\ \%)} R\text{—}*OH$$

1    1.5 eq    2 eq $^{18}O_2$: 99.2 atom %             2-$^{18}$O $^{17}O_2$: 55.2 atom %             2-$^{17}$O

| entry | 1 | *O₂ | labeled alcohol | (2-*O) | yield,[a] % | isotope purity[b] atom % |
|---|---|---|---|---|---|---|
| 1 | 1b | $^{18}O_2$ | H$^{18}$O—[sugar with OMe, AcO, OAc, OAc] | (2b-$^{18}$O) | 88 | >85 |
| 2 | 1b | $^{17}O_2$ | H$^{17}$O—[sugar with OMe, AcO, OAc, OAc] | (2b-$^{17}$O) | 80 | 55 |
| 3 | 1g | $^{18}O_2$ | Ph—CH₂CH₂—CH($^{18}$OH)—Bu | (2g-$^{18}$O) | 98 | >95 |
| 4 | 1j | $^{18}O_2$ | 1-adamantyl-$^{18}$OH | (2j-$^{18}$O) | 98 | 93 |

[a]Isolated yield.
[b]Determined by FAB-Mass (dir) for 2b-$^{18}$O and 2b-$^{17}$O or by EI-Mass (GC) for 2g-$^{18}$O and, 2j-$^{18}$O.
[c]1.5 equiv of $^{17}O_2$ was used.

EXAMPLE 3

A reaction vessel (30 ml, a two-neck, eggplant type flask) is subjected to nitrogen gas purging and NaBH₃CN (0.5 mmol, 31.4 mg), Bu₂(t-Bu)SnCl (0.0125 mmol, 4.1 mg, 3.5 μl) and tert-butanol (1 ml) are added. Then, 3-iodo-1-phenylheptane (0.25 mmol, 75.5 mg, 57.5 g 1) is added to the solution. The introduction of nitrogen gas is discontinued, a nitrogen gas-filled black butyl rubber balloon is set instead, and oxygen (0.375 mmol, 9 ml) is bubbled into the solution using a syringe. The reaction mixture is then incubated on an oil bath at 60° C. After 24 hours, heating is discontinued and the reaction mixture is diluted with pure water (10 ml) and extracted with ether (15 ml×4). The residue is purified by column chromatography (silica gel 2 g, ethyl acetate/hexane 20%) to provide 1-phenyl-3-heptanol (26.9 mg, 55%). ¹H NMR revealed that the crude product comprised the alcohol/reduced compound/starting compound in a molar ratio of 56/28/16.

What is claimed is:

1. A process for producing an alcohol comprising reacting an organohalogen compound of the formula:

R—X with molecular oxygen in the presence of an organotin compound and a reducing agent, wherein said reacting occurs either in the absence of a radical initiator or in the presence of not more than 0.3 equivalent, based on the organohalogen compound, of a radical initiator to provide an alcohol of the formula:

R—OH wherein R represents an organic residue and X represents a halogen and
wherein the amount of the organotin compound ranges from 0.005~0.5 equivalent, based on the organohalogen compound.

2. The process according to claim 1 wherein the organotin compound is an organotin halide.

3. The process according to claim 2 wherein the organotin compound is a trialkyltin halide and the reducing agent is a borohydride.

4. The process according to claim 1, wherein the organotin compound is used in an amount of 0.005 to 0.5 equivalent based on the organohalogen compound,
the reducing agent is used in an amount of 2 to 5 equivalents based on the organohalogen compound and
the oxygen is used in an amount of 1 to 3 equivalents based on the organohalogen compound.

5. The process according to claim 1, wherein the reaction is carried out in the absence of a radical initiator.

6. The process according to claim 1, wherein the reaction is carried out in the presence of not more than 0.3 equivalent, based on the organohalogen compound, of a radical initiator.

7. The process of claim 1, wherein said reacting is conducted at a temperature ranging from 30–70° C.

8. The process of claim 1, further comprising reacting said organohalogen, said reducing agent, and said organotin compound in the presence of sodium iodide.

* * * * *

UNITED STATES PATENT AND TRADEMARK OFFICE
CERTIFICATE OF CORRECTION

PATENT NO. : 6,271,425 B1
DATED : August 7, 2001
INVENTOR(S) : Nakamura et al.

It is certified that error appears in the above-identified patent and that said Letters Patent is hereby corrected as shown below:

Title page,
Item [86], the PCT information should read:

-- [86] PCT No.: PCT/JP98/00453

§ 371 Date: Sep. 7, 1999

§ 102(e) Date: Sep. 7, 1999 --

Signed and Sealed this

Second Day of April, 2002

Attest:

JAMES E. ROGAN
*Attesting Officer*  *Director of the United States Patent and Trademark Office*